(12) United States Patent
Sharpless et al.

(10) Patent No.: US 8,877,939 B2
(45) Date of Patent: *Nov. 4, 2014

(54) COPPER-CATALYSED LIGATION OF AZIDES AND ACETYLENES

(71) Applicant: The Scripps Research Institute, La Jolla, CA (US)

(72) Inventors: K. Barry Sharpless, La Jolla, CA (US); Valery Fokin, Oceanside, CA (US); Vsevold A. Rostovtsev, Wilmington, DE (US); Luke Green, Basel (CH); Fahmi Himo, Solna (SE)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/078,106

(22) Filed: Nov. 12, 2013

(65) Prior Publication Data

US 2014/0066632 A1  Mar. 6, 2014

Related U.S. Application Data

(63) Continuation of application No. 13/412,270, filed on Mar. 5, 2012, now Pat. No. 8,580,970, which is a continuation of application No. 12/804,644, filed on Jul. 26, 2010, now Pat. No. 8,129,542, which is a continuation of application No. 12/152,031, filed on May 9, 2008, now Pat. No. 7,763,736, which is a continuation of application No. 10/516,671, filed as application No. PCT/US03/17311 on May 30, 2003, now Pat. No. 7,375,234.

(60) Provisional application No. 60/385,041, filed on May 30, 2002.

(51) Int. Cl.
*C07D 249/04* (2006.01)
*C07D 249/06* (2006.01)
*C07D 403/06* (2006.01)
*C07D 403/14* (2006.01)
*B01J 31/18* (2006.01)

(52) U.S. Cl.
CPC .......... *C07D 249/04* (2013.01); *B01J 31/1805* (2013.01); *B01J 2531/96* (2013.01); *B01J 2531/16* (2013.01); *B01J 2231/327* (2013.01); *C07D 249/06* (2013.01); *C07D 403/06* (2013.01)
USPC .......................................... 548/255

(58) Field of Classification Search
USPC ........................................ 548/255
See application file for complete search history.

(56) References Cited

U.S. PATENT DOCUMENTS

| | | | |
|---|---|---|---|
| 3,985,765 A | 10/1976 | Buckler et al. | |
| 4,098,894 A | 7/1978 | Buchel et al. | |
| 5,681,904 A | 10/1997 | Manzara | |
| 6,664,399 B1 | 12/2003 | Subramaniam | |
| 7,259,141 B2 | 8/2007 | Thorson | |
| 7,375,234 B2 * | 5/2008 | Sharpless et al. | 548/255 |
| 7,763,736 B2 * | 7/2010 | Sharpless et al. | 548/255 |
| 8,129,542 B2 * | 3/2012 | Sharpless et al. | 548/255 |
| 8,580,970 B2 * | 11/2013 | Sharpless et al. | 548/255 |
| 2001/0011137 A1 | 8/2001 | Urbahns et al. | |
| 2005/0080270 A1 | 4/2005 | Yasuda et al. | |
| 2006/0128766 A1 | 6/2006 | Erik | |
| 2007/0224695 A1 | 9/2007 | Wang et al. | |

OTHER PUBLICATIONS

L'Abbe, "Are Azidocumulenes Accessible?," Bull. Soc. Chim. Belg. 93(7): 579-592 (1984).
Kiick et al., "Incorporation of Azides into Recombinant Proteins for Chemoselective Modification by the Staudinger Ligation," Proc. Natl. Acad. Sci. Usa 99: 19-24 (2002).
Chen et al., "Selectivity in an Encapsulated Cycloaddition Reaction," Org. Lett. 4: 327-329 (2002).
Lewis et al., "Click Chemistry in Situ: Acetylcholinesterase as a Reaction Vessel for the Selective Assembly of a ...," Angew. Chem. Int. Ed. Engl. 41: 1053-1057 (2002).
Tornoe et al., "Peptidotriazoles on Solid Phase: [1,2,3]-Triazoles by Regiospecific Cu(I)-Catalyzed 1,3-Dipolar Cycloadditions ...," J.Org.Chem. 67: 3057-3064 (Apr. 2, 2002).
Tornoe et al., "Peptidotriazoles: Cu(I)-Catalyzed ... " in Peptides:Wave of Future, Am. Pep. Society (2001) 263-264, from Proc. 2nd Intl. and 17th Am Peptide Sym. Jun. 9-14, 2001.
Mock et al., "Catalysis by Cucurbituril: The Significance of Bound-Substrate Destabilization for Induced Triazole Formation," J. Org. Chem. 54: 5302-5308 (1989).
Zanirato, P. "Reactivity of Aryl and Heteroaryl Azides with Vinylsilane and Alkynylsilane: Formation of C-Silylated 1,2,3-...," J. Chem. Soc. Perkin Trans 1: 2789-2796 (1991).
Padwa, A., "Intermolecular 1,3-Dipolar Cycloadditions," in Comprehensive Organic Chemistry, Trost, B., ed., 1069-1109, (1991).

(Continued)

*Primary Examiner* — Joseph Kosack
(74) *Attorney, Agent, or Firm* — Olson & Cepuritis, Ltd.

(57) ABSTRACT

A copper catalyzed click chemistry ligation process is employed to bind azides and terminal acetylenes to provide 1,4-disubstituted 1,2,3-triazole triazoles. The process comprises contacting an organic azide and a terminal alkyne with a source of reactive Cu(I) ion in human blood plasma to form by cycloaddition a 1,4-disubstituted 1,2,3-triazole. The source of reactive Cu(I) ion can be, for example, a Cu(I) salt, Cu(II) ion in the presence of a reducing agent, or copper metal.

20 Claims, 9 Drawing Sheets

(56) References Cited

OTHER PUBLICATIONS

Hlasta et al., "Steric Effects on the Regioselectivity of an Azide-Alkyne Dipolar Cycloaddition Reaction: The Synthesis of Human . . . ," J. Org. Chem. 59: 6184-6189 (1994).

Clarke et al., "Preparation and Pyrolysis of 1-(pyrazol-5-yl)-1,2,3-triazoles and Related Compounds," J. Chem. Soc. Perkin Trans 1: 1799-1804 (1997).

Booth et al., "Efficient Recognition-Induced Acceleration of a [3+2] Dipolar Cycloaddition Reaction," Tetrahedron Lett. 39: 6987-6990 (1998).

Gothelf et al., "Asymmetric 1,3-Dipolar Cycloaddition Reactions," Chem. Rev. 98: 863-909 (1998).

Saxon et al., Cell Surface Engineering by a Modified Staudinger Reaction, Science 287: 2007-2010 (2000).

Cao et al., "Molecular Shuttles by the Protecting Group Approach," J. Org. Chem. 65: 1937-1946 (2000).

Schindler, S., "Reactivity of Copper(I) Complexes Towards Dioxygen," Eur. J. Inorg. Chem. 2311-2326 (2000).

Kolb et al., "Click Chemistry: Diverse Chemical Function from a Few Good Reactions," Angew. Chem. Int. Ed. Engl. 40: 2004-2021 (2001).

Tornoe et al., "Regiospecific Copper(I)-Catalyzed . . . " poster believed to have been presented at Proc. Of Second Intl. And 17th Am. Peptide Symp., (Jun. 9-14, 2001).

Tornoe et al., "Peptidotriazoles: Copper(I)-Catalyzed 1,3-Dipolar Cycloadditions on Solid Phase," Chemical Abstracts 138:385696, (2002).

Rostovtsev et al.,"Stepwise Huisgen Cycloaddition Process:Cu(I)-Catalyzed Regioselective Ligation of Azides and Terminal . . . ," Angew.Chem.Int.Ed. 41: 2596-2599 (2002).

* cited by examiner

Figure 3A

| Entry | Product | yield, % |
|---|---|---|
| 1 | (benzyl 2-(4-phenyl-1H-1,2,3-triazol-1-yl)acetate) | 94 |
| 2 | (2,2-bis((4-phenyl-1H-1,2,3-triazol-1-yl)methyl)propane-1,3-diol) | 93 |
| 3 | (2-(4-phenyl-1H-1,2,3-triazol-1-yl)cyclohexanol) | 82 |
| 4 | (1-(adamantan-1-yl)-4-phenyl-1H-1,2,3-triazole) | 84 |
| 5 | (3-(4-phenyl-1H-1,2,3-triazol-1-yl)benzenesulfonamide) | 92 |

| Entry | Product | yield, % |
|---|---|---|
| 6 |  | 92 |
| 7 |  | 84 |
| 8 |  | 88 |
| 9 |  | 90 |
| 10 |  | 80 |
| 11 |  | 94 |

Facile derivatization of complex molecules: Erythromycin

Polyvalency: exemplary polyazide cores

Polyvalency: exemplary alkyne cores

COPPER-CATALYSED LIGATION OF AZIDES AND ACETYLENES

CROSS-REFERENCE TO RELATED APPLICATIONS

This application is a of continuation of U.S. Ser. No. 13/412,270, filed on Mar. 5, 2012, now U.S. Pat. No. 8,580,970, which is a continuation of U.S. Ser. No. 12/804,644, filed on Jul. 26, 2010, now U.S. Pat. No. 8,129,542, which is a continuation of U.S. Ser. No. 12/152,031, filed on May 9, 2008, now U.S. Pat. No. 7,763,736, which is a continuation of U.S. Ser. No. 10/516,671, filed on May 16, 2005, now U.S. Pat. No. 7,375,234, which is the National Stage of PCT/US2003/17311, filed on May 30, 2003, which claims the benefit of U.S. Provisional Application Ser. No. 60/385,041, filed on May 30, 2002, each of which is incorporated herein by reference in its entirety.

STATEMENT OF GOVERNMENT RIGHTS

This invention was made with government support under Contract No. GM 28384 by the National Institutes of Health and Contract No. CHE-9985553 by the National Science Foundation. The U.S. government has certain rights in this invention.

FIELD OF THE INVENTION

The invention relates to a stepwise Huisgen cycloaddition process catalyzed by copper(I). More particularly, the invention relates to a copper catalysed regioselective click chemistry ligation of azides and terminal alkynes to form triazoles.

BACKGROUND

Huisgen 1,3-dipolar cycloadditions are exergonic fusion processes that unite two unsaturated reactants (R. Huisgen, in 1,3-*Dipolar Cycloaddition Chemistry*, (Ed.: A. Padwa), Wiley, New York, 1984, pp. 1-176; and A. Padwa, in *Comprehensive Organic Synthesis*, (Ed.: B. M. Trost), Pergamon, Oxford, 1991, Vol. 4, pp 1069-1109). For a review of asymmetric 1,3-dipolar cycloaddition reactions, see K. V. Gothelf, et al., *Chem. Rev.* 1998, 98, 863-909. For a review of synthetic applications of 1,3-dipolar cycloadditions, see J. Mulzer, *Org. Synth. Highlights* 1991, 77-95. Huisgen 1,3-dipolar cycloadditions provide fast access to an enormous variety of 5-membered heterocycles (a) W.-Q. Fan, et al., in *Comprehensive Heterocyclic Chemistry II*, (Eds.: A. R. Katritzky, et al.), Pergamon, Oxford, 1996, Vol. 4, pp. 101-126; b) R. N. Butler, in *Comprehensive Heterocyclic Chemistry II*, (Eds.: A. R. Katritzky, et al.), Pergamon, Oxford, 1996, Vol. 4, pp 621-678; and c) K. Banert, *Chem. Ber.* 1989, 122, 911-918). The cycloaddition of azides and alkynes to give triazoles is arguably the most useful member of this family (a) R. Huisgen, *Pure Appl. Chem.* 1989, 61, 613-628; b) R. Huisgen, et al., *Chem. Ber.* 1967, 100, 2494-2507; c) W. Lwowski, in 1,3-*Dipolar Cycloaddition Chemistry*, (Ed.: A. Padwa), Wiley, New York, 1984; Vol. 1, Chapter 5; d) J. Bastide, et al., *Bull. Soc. Chim. Fr.* 1973, 2555-2579; 2871-2887). However, probably because of concerns about the safety of working with organic azides, synthetic chemists, in both pure and applied fields, have not given this transformation the special attention it deserves. Although the actual cycloaddition step may be faster and/or more regioselective for 1,3-dipoles other than azide, the latter is by far the most convenient to introduce and to carry hidden through many synthetic steps. Indeed, it appears to be the only three-atom dipole which is nearly devoid of side reactions.

Azides make only a fleeting appearances in organic synthesis, serving as one of the most reliable means to introduce a nitrogen substituent —R—X→[R—$N_3$]→R—$NH_2$. The azide intermediate is shown in brackets because it is generally reduced straightaway to the amine. Applications which leverage the unique reactivity offered by the azide group itself are disclosed by the following references from the laboratories of Aube, Banert, and Stoddart (a) P. Desai, et al., *J. Am. Chem. Soc.* 2000, 122, 7226-7232; b) K. Banert, *Targets in Heterocyclic Systems* 1999, 3, 1-32; K. Banert, *Liebigs Ann./Recl.* 1997, 2005-18; c) J. Cao, et al., *J. Org. Chem.* 2000, 65, 1937-46 and references cited therein. Although azide chemistry can be hazardous, the hazard of working with these reagents may be minimized by employing appropriate safety precautions. Azides are chemically important as a crucial functional group for click chemistry (H. C. Kolb, et al., *Angew. Chem. Int. Ed.* 2001, 40, 2004-2021). The uniqueness of azides for click chemistry purposes arises from the extraordinary stability of these reagents toward $H_2O$, $O_2$, and the majority of organic synthesis conditions. Indeed, organic azides, particularly in the aliphatic series, are exceptionally stable toward the common reactive chemicals, ranging from dioxygen and water to the aqueous solutions of highly-functionalized organic molecules which make up living cells. (E. Saxon, et al., *Science* 2000, 287, 2007-2010; and K. L. Kiick, et al., *Proc. Natl. Acad. Sci. USA* 2002, 99, 19-24). The spring-loaded nature of the azide group remains invisible unless a good dipolarophile is favorably presented.

In fact, it was the razor sharp reactivity window for this cycloaddition process which spawned our "in situ click chemistry" ideas—an approach which resulted in discovery of the most potent non-covalent inhibitor of acetylcholinesterase known to date. (W. G. Lewis, et al., *Angew. Chem. Int. Ed.* 2002, 41, 1053-1057). However, even then the desired triazole-forming cycloaddition may require elevated temperatures and, in any case, usually results in a mixture of the 1,4- and 1,5-regioisomers (FIG. 1A), unless the acetylene component is attached to an electron-withdrawing group such as a carbonyl or perfluoroalkyl (J. Bastide, et al., *Bull. Chim. Soc. Fr.* 1973, 2294-2296; N. P. Stepanova, et al., *Zh. Org. Khim.* 1985, 21, 979-983; N. P. Stepanova, et al., *Zh. Org. Khim.* 1989, 25, 1613-1618; and D. Clarke, et al., *J. Chem. Soc. Perkin Trans.* 1 1997, 1799-1804).

Efforts to control this 1,4-versus 1,5-regioselectivity problem have met with varying success (P. Zanirato, *J. Chem. Soc. Perkin Trans.* 1 1991, 2789-2796; D. J. Hlasta, et al., *J. Org. Chem.* 1994, 59, 6184-6189; C. A. Booth, et al., *Tet. Lett.* 1998, 39, 6987-6990; S. J. Howell, et al., *Tetrahedron* 2001, 57, 4945-4954; W. L. Mock, et al., *J. Org. Chem.*, 1989, 54, 5302-5308; W. L. Mock *Top. Curr. Chem.* 1995, 175, 1-24; J. Chen, et al., *Org. Lett.* 2002, 4, 327-329; J. W. Wijnen, et al., *Tet. Lett.* 1995, 36, 5389-5392; M. P. Repasky, et al., *Faraday Discuss.* 1998, 110, 379-389).

In one report, copper (I) catalyzed regiospecific synthesis of peptidotriazoles was achieved in organic solvents using free azides and terminal acetylenes attached to a solid support. (C. W. Tornøe, et al., *J. Org. Chem.* 2002, 67, 3057). Reactants were non-equimolar. An earlier report disclosed the formation, in the presence of copper (I), of a triazole, as a low yield byproduct, from a bifunctional reagent having an acetylene group and an in situ generated azide (G. L'abbe, Bull. Soc. Chim. Belg. 1984, 93, 579-592).

SUMMARY OF THE INVENTION

One aspect of the invention is directed to a process for catalyzing a click chemistry ligation reaction between a first reactant having a terminal alkyne moiety and second reactant having an azide moiety for forming a product having a triazole moiety. More particularly, the click chemistry ligation reaction is catalyzed by an addition of Cu(II) in the presence of a reducing agent for reducing said Cu(II) to Cu(I), in situ, in catalytic amount. Preferred reducing agents include ascorbate, metallic copper, quinone, hydroquinone, vitamin $K_1$, glutathione, cysteine, $Fe^{2+}$, $Co^{2+}$, and an applied electric potential. Further preferred reducing agents include metals selected from the group consisting of Al, Be, Co, Cr, Fe, Mg, Mn, Ni, and Zn.

In an alternative aspect of the invention, a click chemistry ligation reaction between a first reactant having a terminal alkyne moiety and second reactant having an azide moiety for forming a product having a triazole moiety is catalyzed by performing the click chemistry ligation reaction in a solution in contact with metallic copper. The metallic copper contributes directly or indirectly to the catalysis of the click chemistry ligation reaction. In a preferred mode, the solution is an aqueous solution. The first and second reactants may be present during the click chemistry ligation reaction in equimolar amounts. Also, the click chemistry ligation reaction may be performed in a solution in contact, at least in part, with a copper vessel.

In another aspect of the invention, a click chemistry ligation reaction between a first reactant having a terminal alkyne moiety and second reactant having an azide moiety for forming a product having a triazole moiety is catalyzed by an addition of a catalytic amount of a metal salt having a metal ion selected from the group consisting of Au, Ag, Hg, Cd, Zr, Ru, Fe, Co, Pt, Pd, Ni, Rh, and W. In a preferred mode of this aspect of the invention, the click chemistry ligation reaction is performed in the presence of a reducing agent for reducing said metal ion to a catalytically active form. Preferred reducing agents include ascorbate, quinone, hydroquinone, vitamin $K_1$, glutathione, cysteine, $Fe^{2+}$, $Co^{2+}$, an applied electric potential, and a metal selected from the group consisting of Al, Be, Co, Cr, Fe, Mg, Mn, Ni, and Zn.

In another aspect of the invention, a click chemistry ligation reaction between a first reactant having a terminal alkyne moiety and second reactant having an azide moiety for forming a product having a triazole moiety is performed in an aqueous solution and is catalyzed by a catalytic amount of copper (I). In a preferred mode of this aspect of the invention, the first and second reactants are present in equimolar amounts.

In another aspect of the invention, a click chemistry ligation reaction between a first reactant having a terminal alkyne moiety and second reactant having an azide moiety for forming a product having a triazole moiety is catalyzed by a catalytic amount of copper (I) while the first and second reactants are present in equimolar amounts. In a preferred mode of this aspect of the invention, the click chemistry ligation reaction is performed in an aqueous solution.

In another aspect of the invention, a click chemistry ligation reaction between a first reactant having a terminal alkyne moiety and second reactant having an azide moiety for forming a product having a triazole moiety is performed in a solution containing a catalytic amount of copper (I). However, in this instance, there is a proviso that either the first or second reactant is toxic or expensive and the remaining reactant is present in molar excess.

In another aspect of the invention, a click chemistry ligation reaction between a first reactant having a terminal alkyne moiety and second reactant having an azide moiety for forming a product having a triazole moiety is performed inside a cell. The cell is of a type that contains a catalytic quantity of copper(I) sufficient to catalyze the click chemistry ligation reaction. The copper(I) contributes to a catalysis of the click chemistry ligation reaction.

In another aspect of the invention, a click chemistry ligation reaction between a first reactant having a terminal alkyne moiety and second reactant having an azide moiety for forming a product having a triazole moiety is performed in a solvent containing a catalytic amount of a metal ion. The metal ions are selected from the group of metals consisting of Cu, Au, Ag, Hg, Cd, Zr, Ru, Fe, Co, Pt, Pd, Ni, Rh, and W. The metal ion contributes directly or indirectly to a catalysis of the click chemistry ligation reaction. The metal ion is coordinated to a ligand for solubilizing such metal ion within the solvent, for inhibiting oxidation of such metal ion, and for dissociating, in whole or in part, from such metal ion during the catalysis of the click chemistry ligation reaction by said metal ion. A preferred ligand is acetonitrile. Another preferred ligand is a cyanide, nitrile, or isonitrile. Another preferred ligand is water. Other preferred ligands include nitrile, isonitrile, primary, secondary, or tertiary amine, a nitrogen bearing heterocycle, carboxylate, halide, alcohol, thiol, sulfide, phosphine, and phosphite. Other preferred ligands are polyvalent and include one or more functional groups selected from the group consisting of nitrile, isonitrile, primary, secondary, or tertiary amine, a nitrogen bearing heterocycle, carboxylate, halide, alcohol, thiol, sulfide, phosphine, and phosphite.

Another aspect of the invention is directed to a reactive intermediate for producing a product having triazole moiety. The reactive intermediate is represented by the following 6-membered ring structure:

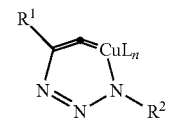

In the above structure, $R^1$ is a 4-triazole substituent, $R^2$ is a 1-triazole substituent, L is a Cu ligand, and "n" is 1, 2, or 3.

Another aspect of the invention is directed to a reactive intermediate for producing a triazole. The reactive intermediate is represented by the following 6-membered ring structure:

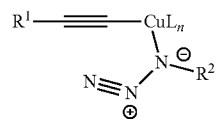

In the above structure, $R^1$ is employable as a 4-triazole substituent, $R^2$ is employable as a 1-triazole substituent, L is a Cu ligand, and "n" is 1, 2, 3, or 4.

Another aspect of the invention is directed to a two step process of derivatizing an amine containing molecule with a triazole. In the first step of this process the amine containing molecule is derivatized to form a terminal alkyne. Then, the product of the first step is ligated with an azide containing molecule by addition of the azide containing molecule in the presence of a catalytic amount of Cu to form a triazole derivative of the amine containing molecule.

Another aspect of the invention is directed to one step process for producing a polyvalent triazole. In this process, a polyazide core is derivatized by addition of a molecule having a terminal alkyne in the presence of a catlytic amount of Cu.

Another aspect of the invention is directed to a one step process for producing a polyvalent triazole. In this process, a polyalkyne core is derivatized by addition of an azide containing molecule in the presence of a catalytic amount of Cu.

BRIEF DESCRIPTION OF THE DRAWINGS

FIGS. 3A and 3B illustrate a table showing the synthesis of 1,4-disubstituted [1,2,3]-triazoles catalyzed by $Cu^I$ in the presence of ascorbate. All reactions were carried out in water with t-butanol as co-solvent, 0.25-0.5M in reactants, with 1 mol % of $CuSO_4$ and 10 mol % of sodium ascorbate, and were complete in 12-24 hours.

DETAILED DESCRIPTION

The process is experimentally simple and appears to have enormous scope. While a number of copper(I) sources can be used directly (vide infra), it is disclosed that the catalyst is better prepared in situ by reduction of $Cu^{II}$ salts, which are less costly and often purer than $Cu^I$ salts ($CuSO_4.5H_2O$ serves well). As the reductant, ascorbic acid and/or sodium ascorbate proved to be excellent, for they allow preparation of a broad spectrum of 1,4-triazole products in high yields and purity at 0.25-2 mol % catalyst loading. For a review of reactions of L-ascorbic acid with transition metals see M. B. Davies *Polyhedron* 1992, 11, 285-321 and references cited therein; redox properties of ascorbic acid are summarized in C. Creutz *Inorg. Chem.* 1981, 20, 4449. The reaction appears to be very forgiving and does not require any special precautions. It proceeds to completion in 6 to 36 hours at ambient temperature in a variety of solvents, including aqueous t-butanol or ethanol and, very importantly, water with no organic co-solvent. Starting materials do not need to be dissolved in the reaction solvent. The reaction seems to proceed just as efficiently as long as adequate stirring is maintained. Although most experiments were performed at near neutral pH, the catalysis seems to proceed well at pH values ranging from ca. 4 to 12. The catalytic process is very robust and insensitive to usual reaction parameters.

It is further disclosed that $Cu^0$ can also be used as a source of the catalytic species. Although these reactions may take longer to proceed to completion, the experimental procedure is exceedingly simple. For example, bis-triazole shown in entry 2 (FIG. 3A) was obtained in quantitative yield after stirring the corresponding azide and acetylene components for 24 h with ca. 2 g of copper metal turnings. The turnings were removed at the end of the reaction, and the pure white product was collected by simple filtration.

The reaction between phenyl propargyl ether and benzylazide in the presence of 5 mol % of sodium ascorbate and 1 mol % of copper(II) sulfate in 2:1 water/t-butanol mixture furnished the 1,4-disubstituted triazole product in 91% yield after stirring for 8 hours at room temperature in a capped scintillation vial, but otherwise with no effort to exclude oxygen [eq. (2)]. The regiochemistry of the product was established by NOE experiments and confirmed by the X-ray crystallographic analysis.

Figure 1A:
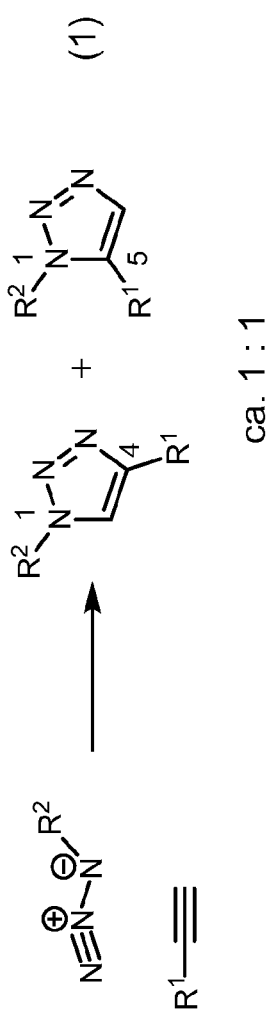
FIG. 1A illustrates a prior art uncatalysed Huisgen cycloaddition of azides and terminal alkynes.
Figure 1B:
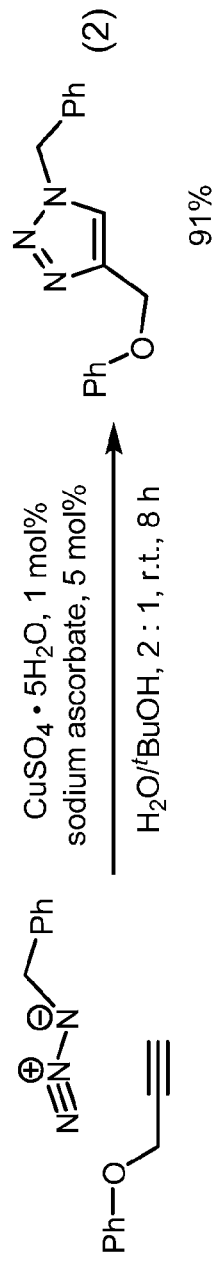
FIG. 1B illustrates a copper catalysed regioselective ligation of azides and terminal alkynes.

For comparison, the thermal reaction (neat, 92° C., 18 h) between these substrates gives both regioisomers in a ratio of 1.6:1 in favor of the 1,4-isomer, as illustrated in FIG. 1A.

Figure 3B:
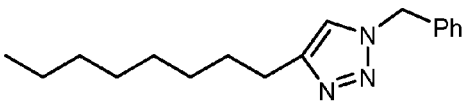
Figure 3B:
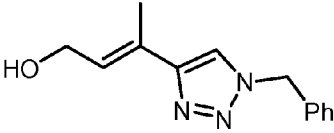
Figure 3B:
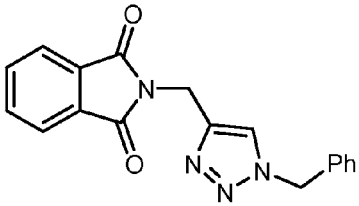
Figure 3B:
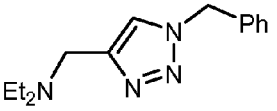
Figure 3B:
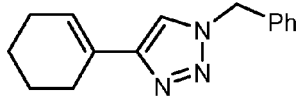
Figure 3B:
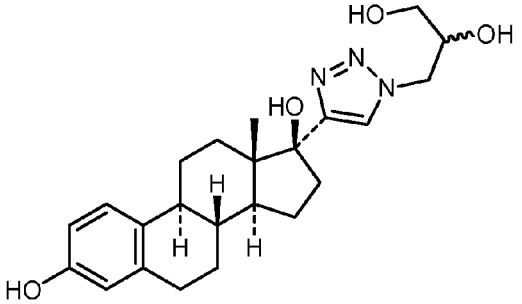
Figure 4:
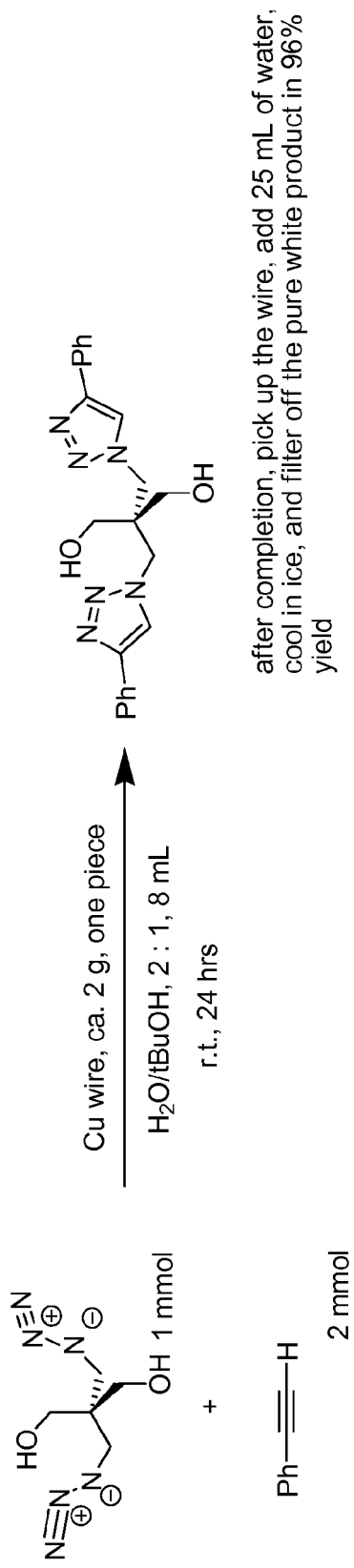
FIG. 4 illustrates copper catalysed regioselective ligation of azides and terminal alkynes employing Cu(0) as a reducing agent to reduce Cu(2) to Cu(1).
Figure 5:
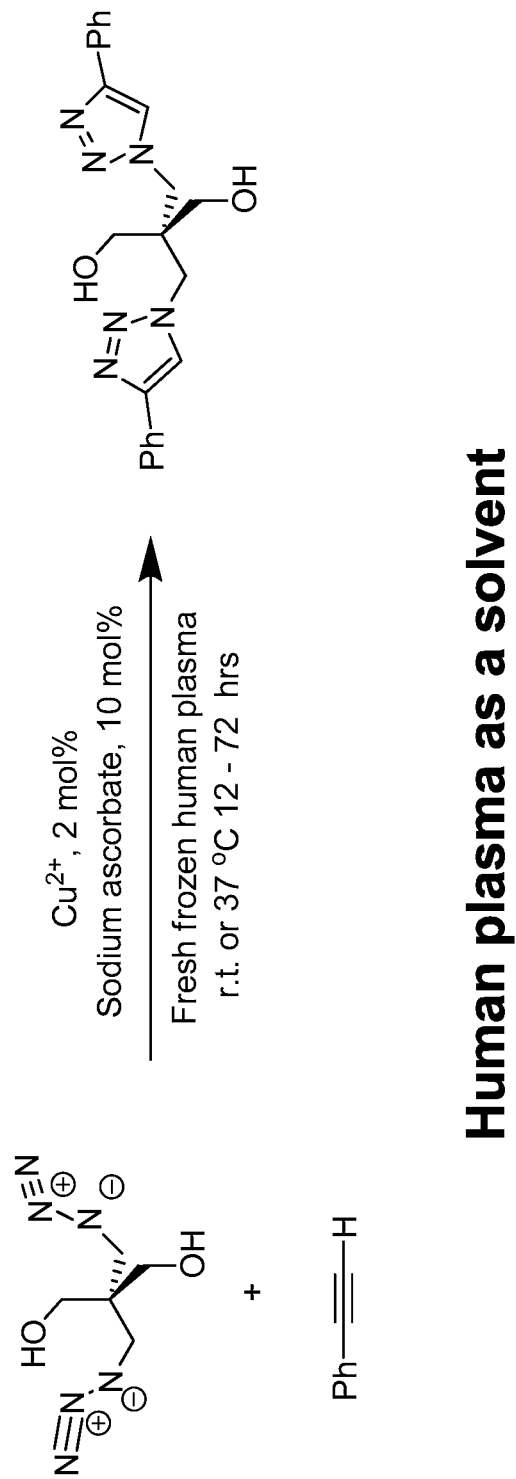
FIG. 5 illustrates use of human plasma as a solvent for the reaction. At 100 mM azide and 200 mM acetylene, the reaction is complete in 12-14 hours. At 2 mM azide and 4 mM acetylene, the reaction is approximately 80% complete after 48 hours. Note that the reaction does not decline in plasma, but merely slows down. Despite the high concentration of proteins and the binding of Cu to protein, the reaction proceeds well.

The scope of this copper-catalyzed triazole synthesis is partly revealed by the examples in FIGS. 3A and B; note especially the lack of functional group interference. These triazoles are obtained using a procedure which generally involves little more than stirring the reagents and filtering off pure products. Variously substituted primary, secondary, tertiary, and aromatic azides readily participate in this transformation. Tolerance for variations in the acetylene component is also excellent.

Copper(I) salts, for example CuI, $CuOTf.C_6H_6$ and [Cu$(NCCH_3)_4$]$PF_6$, can also be used directly in the absence of a reducing agent. These reactions usually require acetonitrile as co-solvent and one equivalent of a nitrogen base (e.g. 2,6-lutidine, triethylamine, diisopropylethylamine, or pyridine). However, formation of undesired byproducts, primarily diacetylenes, bis-triazoles, and 5-hydroxytriazoles, was often observed. For a recent summary of the reactions of copper(I) complexes with dioxygen, see S. Schindler *Eur. J. Inorg. Chem.* 2000, 2311-2326 and A. G. Blackman, W. B. Tolman in *Structure and Bonding*, B. Meunier, Ed., Springer-Verlag, Berlin, Heidelberg, 2000, vol. 97, p. 179-211. This complication with direct use of $Cu^I$-species was minimized when 2,6-lutidine was used, and exclusion of oxygen further improved product purity and yield. For example, ethylpropiolate and benzyl azide furnished the corresponding 1,4-triazole in 55% yield when this procedure was used, but only trace amount of the product was obtained with 1 equiv. of triethylamine and no exclusion of oxygen. Even though a broad range of both acetylene and azide components react readily in the acetonitrile system, we prefer the even more reliable and simple $Cu^{II}$/ascorbate aqueous system (with or without co-solvents and amine buffers/additives).

Figure 2:
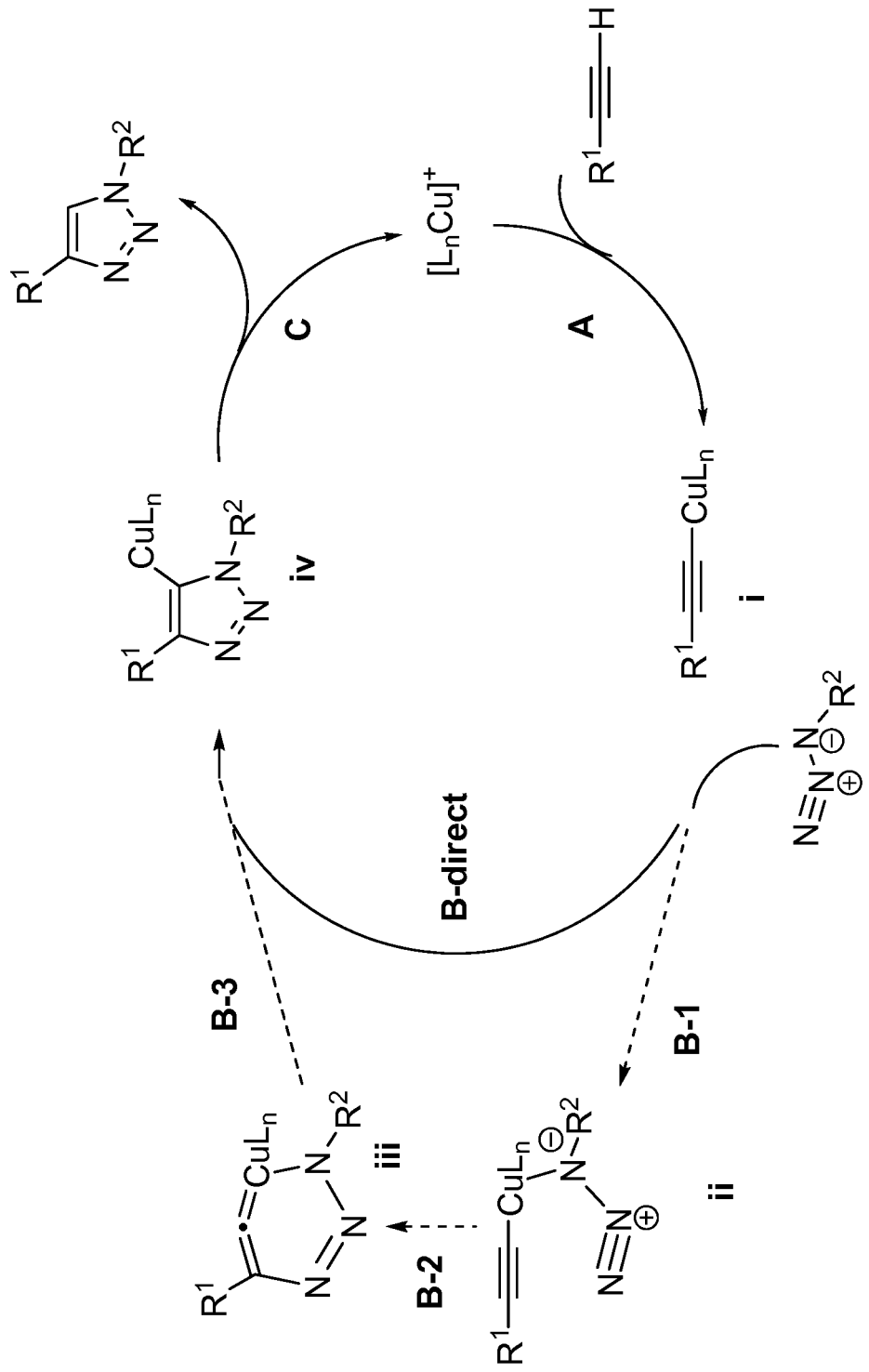
FIG. 2 illustrates proposed mechanism for the step-wise copper catalysed ligation of azides and terminal alkynes and compares this mechanism with a direct cycloaddition.

A mechanistic proposal for the catalytic cycle is illustrated in FIG. 2. It begins unexceptionally with formation of the copper(I) acetylide i (G. van Koten, J. G. Noltes in *Comprehensive Organometallic Chemistry*, G. Wilkinson, Ed., vol. 2, chap. 14, Pergamon Press, 1982, 720). As expected, no reaction is observed with internal alkynes. It is disclosed herein that extensive density functional theory calculations offer compelling evidence which strongly disfavors, by approximately 12-15 kcal, the concerted [2+3] cycloaddition (B-direct) and points to a stepwise, annealing sequence (B1→B2→B3,), which proceeds via the 6-membered copper containing intermediate iii (M. P. Doyle, et al., in *Modern Catalytic Methods for Organic Synthesis with Diazo Compounds* Wiley (New York), 1997, 163-248). Hence, the term 'ligation' is employed herein to denote the step-wise [2+3] cyclicoaddition catalyzed by copper(I).

The $Cu^I$-catalyzed transformation described here—a high-yielding and simple to perform 'fusion' process leading to a thermally and hydrolytically stable triazole connection—is an ideal addition to the family of click reactions. The process exhibits broad scope and provides 1,4-disubstituted [1,2,3]-triazole products in excellent yields and near perfect regioselectivity. The reactivity of copper(I) acetylides with organic azides is disclosed herein to be effectively unstoppable.

Figure 6:
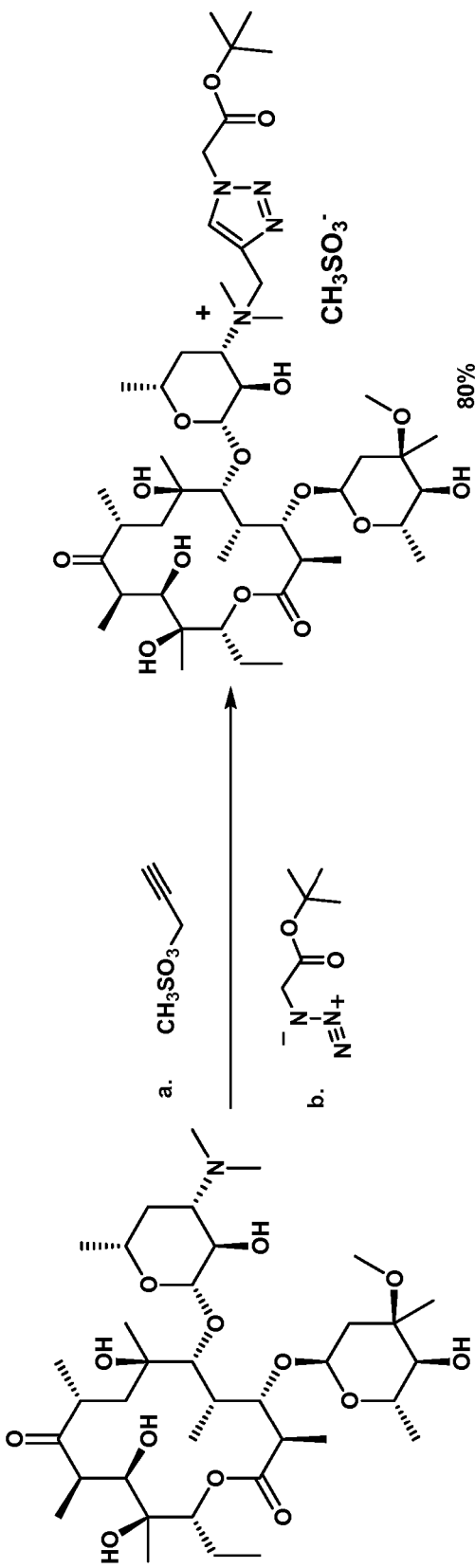
FIG. 6 illustrates an exemplary two step procedure for derivatizing amine containing molecules, e.g. erythromycin, with triazoles. The procedure is applicable to any amine containing molecule.
Figure 7:
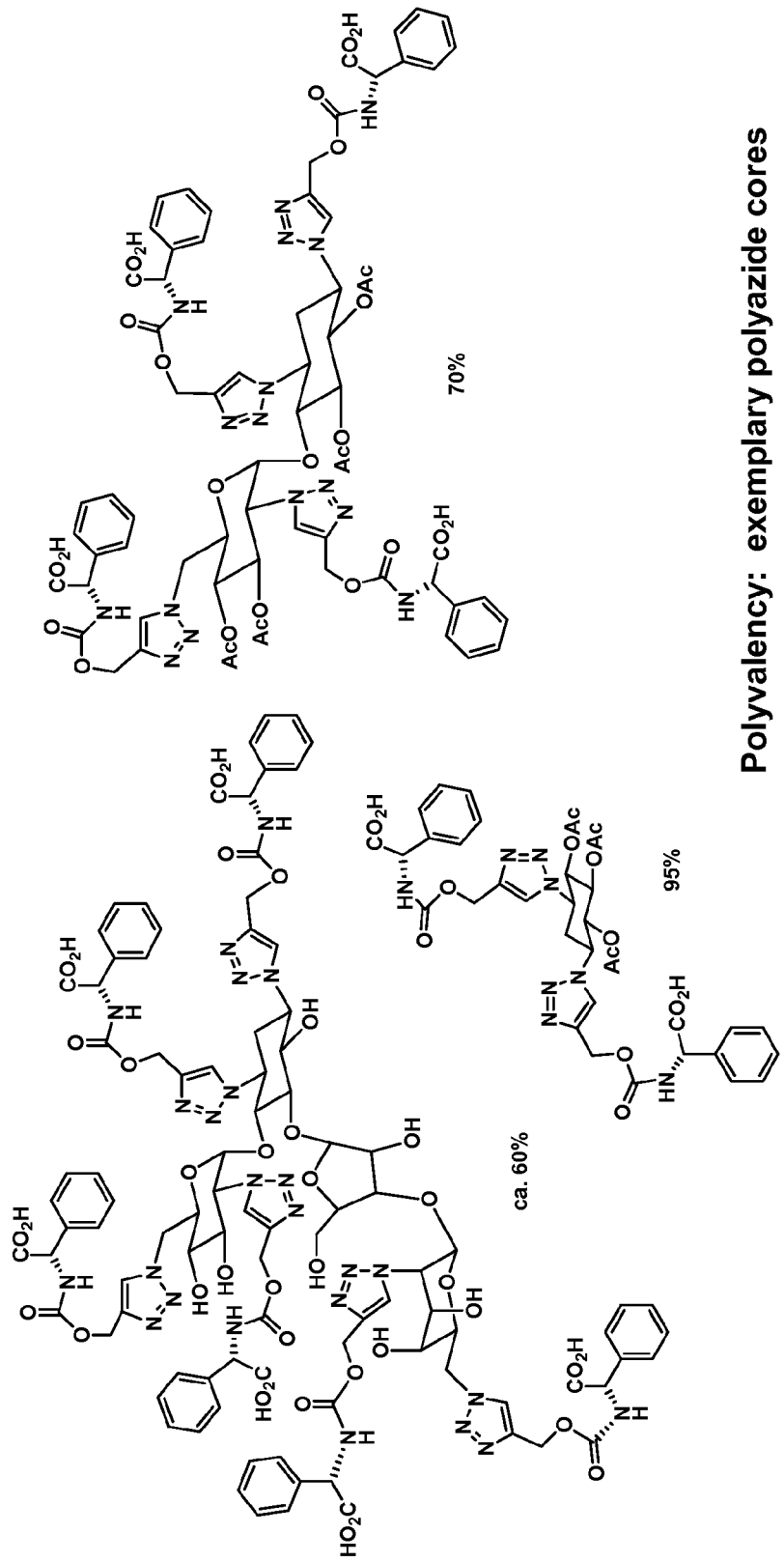
FIG. 7 illustrates a one step process using Cu catalysis for derivatizing polyazide cores to produce polyvalent triazoles.
Figure 8:
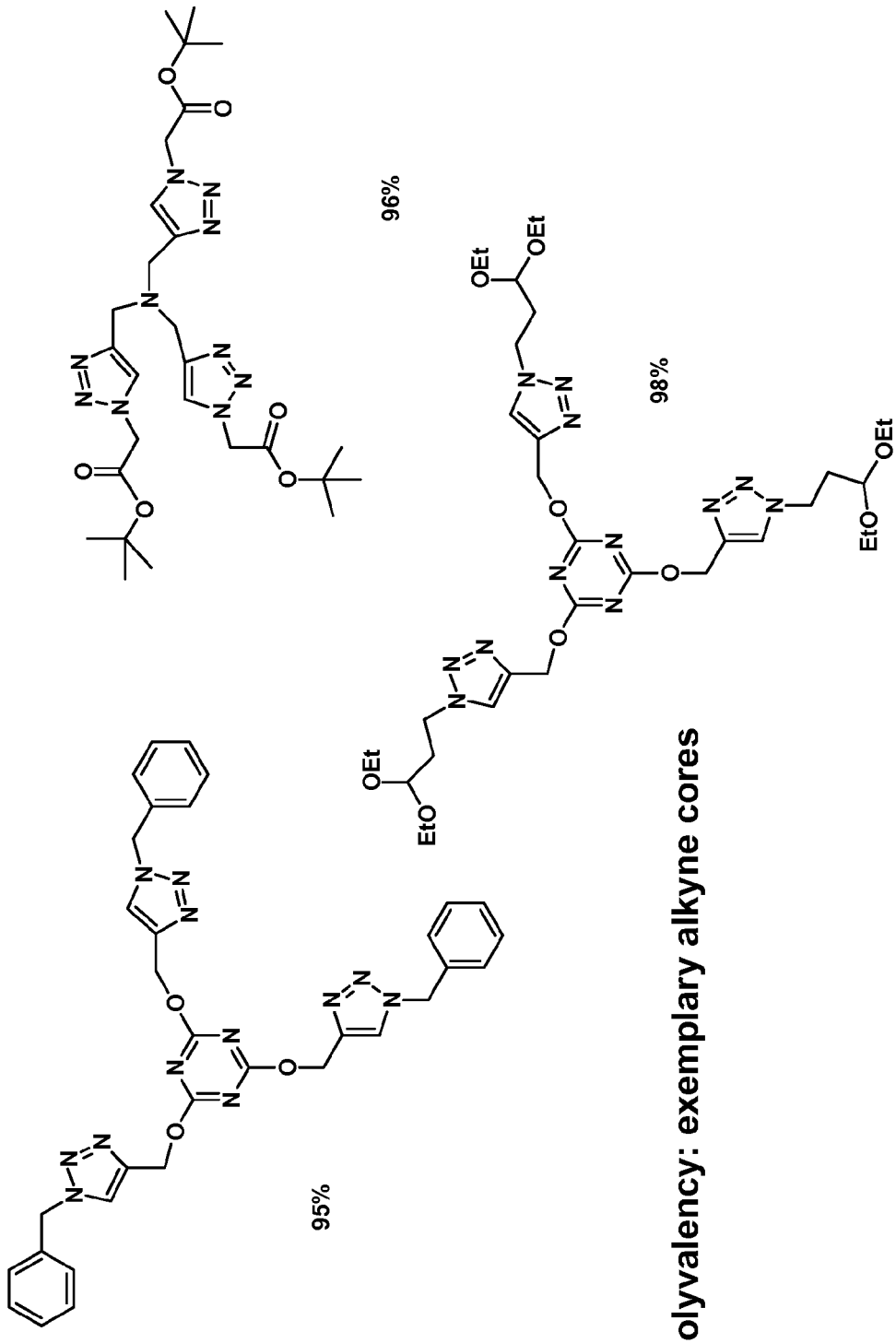
FIG. 8 illustrates a one step process using Cu catalysis for derivatizing polyalkyne cores to produce polyvalent triazoles.

This new catalytic process offers an unprecedented level of selectivity, reliability and scope for those organic synthesis endeavors which depend on the creation of covalent links between diverse building blocks. Several applied projects which highlight the capabilities of the process are illustrated in FIGS. 6-8.

Experimental Procedure

General Procedure as Exemplified for the Synthesis of 17-[1-(2,3-Dihydroxypropyl)-1H-[1,2,3]-triazol-4-yl]-estradiol 17-ethynyl estradiol (888 mg, 3 mmol) and (S)-3-azidopropane-1,2-diol (352 mg, 3 mmol) were suspended in 12 mL of 1:1 water/t-butanol mixture. Sodium ascorbate (0.3 mmol, 300 µL, of freshly prepared 1M solution in water) was added, followed by copper(II) sulfate pentahydrate (7.5 mg, 0.03 mmol, in 100 µL, of water). The heterogeneous mixture was stirred vigorously overnight, at which point it cleared and TLC analysis indicated complete consumption of the reactants. The reaction mixture was diluted with 50 mL of water, cooled in ice, and the white precipitate was collected by filtration. After washing with cold water (2×25 mL), the precipitate was dried under vacuum to afford 1.17 g (94%) of pure product as off-white powder. M.p. 228-230° C. Elemental analysis calculated: C, 64.02%; H, 7.71%; N, 9.74%. found C, 64.06%; H, 7.36%; N, 9.64%.

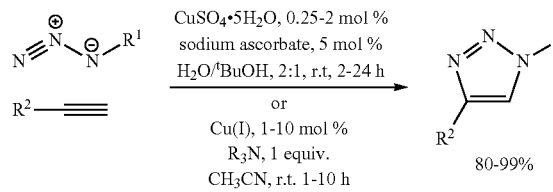

Reducing Environment Effect:

Cu(I) is very easily oxidized to Cu(II)—primarily by oxygen, but even milder oxidants can accomplish this. Additionally, Cu(I) mediates oxidative coupling of acetylenes and other organocopper species, which leads to reduced yields and contaminated products. All these problems can be circumvented by the use of a mild reducing agent. Various reducing agents can be used: ascorbate, hydroquinone, other quinones (such as vitamin $K_1$), copper turnings/wire, glutathione, cysteine, $Fe^{2+}$, $Co^{2+}$, etc. Virtually any reductant may be employed that is not so powerful so as to rapidly reduce Cu(II) to Cu(0).

Ligands: Acetonitrile Effect:

Metals do not exist in solutions "naked"—there are always ligands present in the coordination sphere, be it solvent molecules or 'designer' ligands. Ligands have a profound effect on reactivity of the metal center, as well as red/ox properties of the metal: (a) they can stabilize a certain oxidation state of the metal, e.g. Cu(I) is the desirable form in our case, and (b) just as importantly, they can keep the catalytic species in the solution, thereby making it constantly available for the catalysis. Both of these requirements have to be fulfilled in order for a metal/ligand combination to be useful in catalyzing a desired transformation cycloaddition, or ligation, in the present instance.

Copper-mediated organic transformations have been studied for over 70 years, and the literature on the subject is quite extensive. An important lesson of the prior art is that cyanides and/or nitriles are some of the best ligands for Cu(I), which is usually tetracoordinated, forming tetrahedral complexes. In fact, acetonitrile coordinates to Cu(I) so strongly that [Cu(CH$_3$CN)$_4$]$^+$PF$_6^-$ complex is a commercially available, oxygen-insensitive Cu(I) preparation (i.e., this Cu(I) is unreactive). This 'overstabilization' is clearly a liability when reactivity is our goal. The reaction indicated below illustrates the point. When water/alcohol mixtures are employed as solvents (note that both are weak ligands for Cu(I)), the reaction is complete in under 6 hrs. However, when acetonitrile is used as a solvent, no reaction is observed at all even after 24 hrs under otherwise identical conditions.

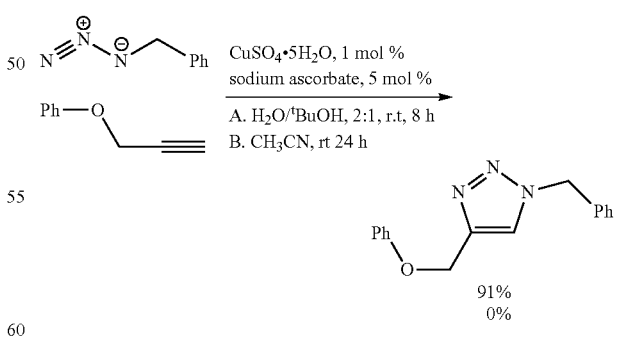

To explain this phenomenon, recall the mechanism of the reaction. In order for the ligation to proceed, the azide must coordinate to the copper (step B1) and one ligand must be removed from the coordination sphere of the metal, and in case of a strongly coordinated acetonitrile, this step is disfavored.

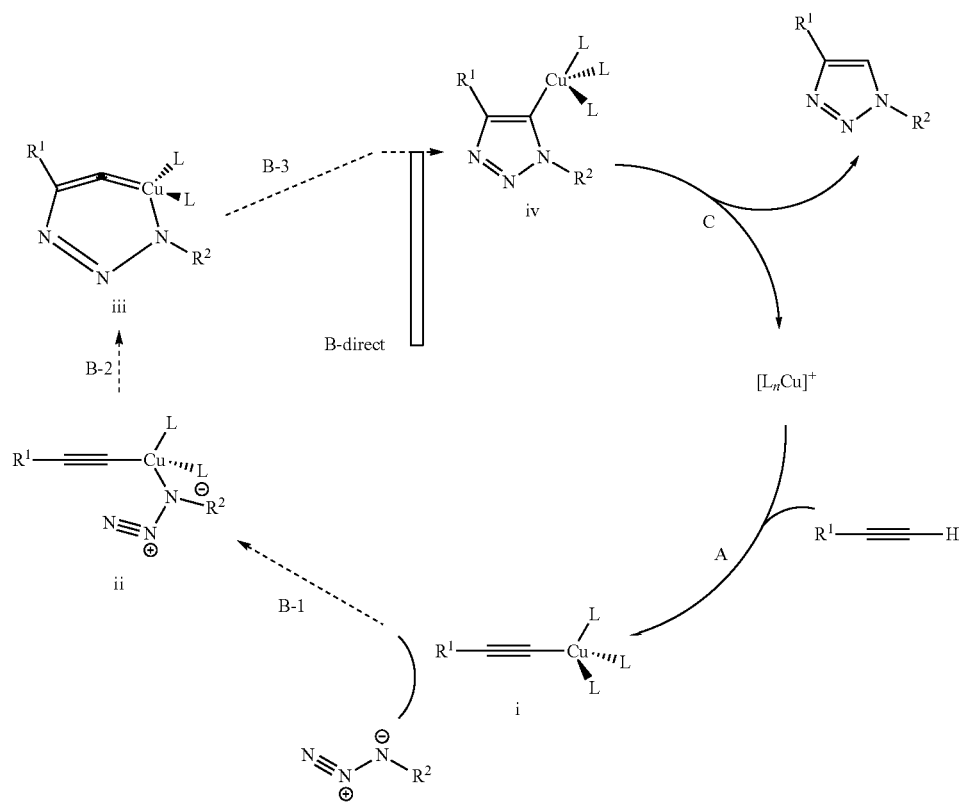

Therefore, in order to have a useful reactivity window, one should choose or design such ligands that do bind to the metal relatively well, keep it in the correct oxidation state and in solution (i.e. not aggregated to the point of forming a polymeric precipitate), but in the same time can come off the metal center to allow formation of intermediate ii, which is a necessary step in the catalytic sequence. To use the example in hand, addition of an amine, such as triethylamine or 2,6-lutidine to the acetonitrile system described above, solves the problem of reactivity—the product is formed in quantitative yield after ca. 8 hrs.

Preferred ligands include cyanides, nitriles, isonitriles, primary or secondary amines, carboxylates, halides, alcohols, and thiols. Chloride is the preferred halide and best employed at 1-5 M. Polyvalent ligands that include one or more functional groups selected from nitrile, isonitrile, primary or secondary amine, carboxylate, alcohol, and thiol may also be employed.

Other Metal Catalysts:

Cu is not the only metal capable of catalyzing this type of cycloaddition. As long as intermediate ii can be formed (i.e. the metal is or can become coordinatively unsaturated), other metals known to form stable acetylides may also be employed. Exemplary metals that can form stable acetylides include Cu, Au, Ag, Hg, Cd, Zr, Ru, Fe, Co, Pt, Pd, Ni, Rh, and W. It is a matter of finding the right metal/ligand combination. Copper is unique among other metals because it is so well supported in aqueous systems, which results in exceedingly simple experimental procedure and amazing functional group tolerance.

Catalysis of Ligation Reaction by Metallic Container:

Metallic containers can also be used as a source of the catalytic species to catalyze the ligation reaction. For example, a copper container ($Cu^0$) may be employed to catalyze the reaction. In order to supply the necessary ions, the reaction solution must make physical contact with the a copper surface of the container. Alternatively, the reaction may be run in a non-metallic container, and the catalyic metal ions supplied by contacting the reaction solution with a copper wire, copper shavings, or other structures. Although these reactions may take longer to proceed to completion, the experimental procedure is exceedingly simple. For example, bis-triazole shown in entry 2 (FIG. 3A) was obtained in quantitative yield after stirring the corresponding azide and acetylene components for 24 h with ca. 2 g of copper metal turnings. The turnings were removed at the end of the reaction, and the pure white product was collected by simple filtration.

Alternative Reducing Agents:

Metals may be employed as reducing agents to maintain the oxidation state of the Cu (I) catalyst or of other metal catalysts. Preferred metallic reducing agents include Cu, Al, Be, Co, Cr, Fe, Mg, Mn, Ni, and Zn. Alternatively, an applied electric potential may be employed to maintain the oxidation state of the catalyst.

In Vivo Catalysis:

The reaction proceeded well in fresh human plasma (protein loading 65-85 mg/mL, $C_{azide}=C_{alkyne}=5$ mM; $C_{Cu+}=100$ mM) and in whole blood, indicating that copper species remained available for the catalysis despite being heavily bound to plasma proteins and indicating that the ligation reaction can be catalyzed by copper and/or other metals ions and templates in vivo, including intracellularly. The reaction proceeds fresh human plasma and intracellularly in whole blood without noticeable loss of catalytic turnover and without noticeable protein precipitation.

Cu(I) Salt Used Directly:

If Cu(I) salt is used directly, no reducing agent is necessary, but acetonitrile or one of the other ligands indicate above should be used as a solvent (to prevent rapid oxidation of Cu(I) to Cu(II) and one equivalent of an amine should be added (to accelerate the otherwise extremely slow reaction—vide supra). In this case, for better yields and product purity, oxygen should be excluded. Therefore, the ascorbate (or any other reducing) procedure is often preferred over the unreduced procedure. The use of a reducing agent is procedurally simple, and furnishes triazole products in excellent yields and of high purity.

What is claimed is:

1. A copper catalyzed process for preparing a 1,4-disubstituted 1,2,3-triazole comprising:
contacting a human blood plasma solution of an organic azide and a terminal alkyne with a source of catalytic Cu(I) ion to form by cycloaddition a 1,4-disubstituted 1,2,3-triazole.

2. The process of claim 1 wherein the solution further comprises at least one ligand comprising at least one functional group selected from the group consisting of a nitrile, an isonitrile, a primary amine, a secondary amine, a tertiary amine, a nitrogen bearing heterocycle, a carboxylate, a halide, an alcohol, a thiol, a sulfide, a phosphine, and a phosphite.

3. The process of claim 1 wherein the solution further comprises at least one polyvalent ligand comprising one or more functional groups selected from the group consisting of a nitrile, an isonitrile, a primary amine, a secondary amine, a tertiary amine, a nitrogen bearing heterocycle, a carboxylate, a halide, an alcohol, a thiol, a sulfide, a phosphine, and a phosphite.

4. The process of claim 1 wherein the source of catalytic Cu(I) ion comprises a Cu(I) salt.

5. The process of claim 1 wherein the source of catalytic Cu(I) comprises Cu(II) ion in combination with a reducing agent.

6. The process of claim 1 wherein the source of catalytic Cu(I) comprises copper metal.

7. A copper catalyzed process for preparing a 1,4-disubstituted 1,2,3-triazole comprising:
contacting an aqueous solution of an organic azide and a terminal alkyne with a source of Cu(I) ion and a ligand for Cu(I) to form a 1,4-disubstituted 1,2,3-triazole, wherein the aqueous solution comprises water and a cosolvent.

8. The process of claim 7 wherein the cosolvent comprises a nitrile.

9. The process of claim 8 wherein the nitrile comprises acetonitrile.

10. The process of claim 1 wherein the cosolvent comprises an alcohol.

11. The process of claim 10 wherein the alcohol comprises ethanol or tert-butanol.

12. The process of claim 7 wherein the ligand comprises one or more functional groups selected from the group consisting of a nitrile, an isonitrile, a primary amine, a secondary amine, a tertiary amine, a nitrogen bearing heterocycle, a carboxylate, a halide, an alcohol, a thiol, a sulfide, a phosphine, and a phosphite.

13. The process of claim 7 wherein the source of Cu(I) ion comprises a Cu(I) salt.

14. The process of claim 7 wherein the source of catalytic Cu(I) comprises Cu(II) ion in combination with a reducing agent.

15. The process of claim 14 wherein the reducing agent comprises ascorbate.

16. The process of claim 14 wherein the Cu(II) ion is provided as a Cu(II) salt.

17. The process of claim 14 wherein the Cu(II) salt comprises $CuSO_4$ or a hydrate thereof.

18. The process of claim 7 wherein the source of catalytic Cu(I) comprises copper metal.

19. A copper catalyzed process for preparing a 1,4-disubstituted 1,2,3-triazole comprising:
contacting an aqueous solution of an organic azide and a terminal alkyne with a source of Cu(I) ion and a ligand for Cu(I) to form a 1,4-disubstituted 1,2,3-triazole, wherein the aqueous solution comprises water and a cosolvent comprising ethanol, acetonitrile, or a combination thereof; and the source of Cu(I) ion comprises a Cu(II) salt and ascorbate.

20. The process of claim 19 wherein the ligand comprises one or more functional groups selected from the group consisting of a nitrile, an isonitrile, a primary amine, a secondary amine, a tertiary amine, a nitrogen bearing heterocycle, a carboxylate, a halide, an alcohol, a thiol, a sulfide, a phosphine, and a phosphite.

* * * * *

UNITED STATES PATENT AND TRADEMARK OFFICE
CERTIFICATE OF CORRECTION

PATENT NO. : 8,877,939 B2  
APPLICATION NO. : 14/078106  
DATED : November 4, 2014  
INVENTOR(S) : Sharpless et al.

Page 1 of 1

It is certified that error appears in the above-identified patent and that said Letters Patent is hereby corrected as shown below:

In the Specification

Column 1, Lines 20-26, the paragraph STATEMENT OF GOVERNMENT RIGHTS should be changed to:
-- STATEMENT OF GOVERNMENT LICENSE RIGHTS
This invention was made with government support under grant number GM028384 awarded by the National Institutes of Health and under grant number CHE9985553 awarded by the National Science Foundation. The government has certain rights in the invention. --

Signed and Sealed this  
Seventh Day of April, 2020

Andrei Iancu  
*Director of the United States Patent and Trademark Office*